United States Patent [19]

Bouras

[11] Patent Number: 5,639,459

[45] Date of Patent: Jun. 17, 1997

[54] COMPOSITIONS FOR TREATMENT OF THE HAIR

[76] Inventor: Elias Bouras, 18 Lucerne Court, Bognor Regis, West Sussex, PO21 4XL, Great Britain

[21] Appl. No.: 464,746

[22] PCT Filed: Jan. 6, 1994

[86] PCT No.: PCT/GB94/00021

§ 371 Date: Jul. 6, 1995

§ 102(e) Date: Jul. 6, 1995

[87] PCT Pub. No.: WO94/15574

PCT Pub. Date: Jul. 21, 1994

[30] Foreign Application Priority Data

| Jan. 11, 1993 | [GB] | United Kingdom | 9300411 |
| Apr. 26, 1993 | [GB] | United Kingdom | 9308572 |
| Jun. 3, 1993 | [GB] | United Kingdom | 9311437 |
| Oct. 1, 1993 | [GB] | United Kingdom | 9320329 |

[51] Int. Cl.$^6$ ............................................. A51K 35/78

[52] U.S. Cl. .................. 424/195.1; 514/70.1; 514/677; 514/682; 514/719; 514/880

[58] Field of Search ..................... 424/195.1, 719, 424/682, 677, 70.1; 514/880

[56] References Cited

FOREIGN PATENT DOCUMENTS

| 888689 | 12/1971 | Canada . |
| 0073173 | 3/1983 | European Pat. Off. . |
| 2347049 | 11/1977 | France . |
| 2436467 | 2/1976 | Germany . |
| 54-6612 | 3/1979 | Japan . |
| 59-139313 | 8/1984 | Japan . |
| 1-233208 | 9/1989 | Japan . |
| 2-247299 | 10/1990 | Japan . |
| 3-258713 | 11/1991 | Japan . |
| 1568856 | 6/1980 | United Kingdom . |
| 91/04007 | 4/1991 | WIPO . |

OTHER PUBLICATIONS

Abstract of JP-A-2-247299.

Abstract of JP-A-1-233208.

Abstract of JP-A-54-6612.

Abstract of JP-A-59-139313.

Abstract of JP-A-3-258713.

*Primary Examiner*—John W. Rollins
*Attorney, Agent, or Firm*—Oliff & Berridge

[57] ABSTRACT

The invention provides a composition for the treatment for the hair, scalp and skin to improve condition and to assist in hair regrowth which comprises a pharmaceutically acceptable oxalate of a group Ia or Ia or ammonium oxalate metal disposed in a pharmaceutically acceptable carrier of diluent therefor. Preferably, the group IIa metal is calcium and the pharmaceutically acceptable carrier or diluent is an ointment.

14 Claims, No Drawings

COMPOSITIONS FOR TREATMENT OF THE HAIR

The present invention relates to topical compositions for the treatment of the hair which comprise a pharmaceutically acceptable oxalate of a group Ia or IIa metal or ammonium oxalate, disposed in a pharmaceutical acceptable carrier or diluent therefor. The pharmaceutically acceptable oxalate is preferably an oxalate selected from calcium, barium or magnesium, lithium, sodium or potassium and may include an organic plant derived oxalate.

Extracts of red and white squill have long been reported to have medicinal properties; white squill having the property of being a cardiac stimulant, a diuretic or emetic. These extracts have been utilised for this purpose for very many years.

We have previously described how both red and white squill extracts are useful for restoring hair loss due to conditions such as alopecia whether or not problems of seborrhoea exist.

The applicant has now found that a significant component of this composition, in so far as hair treatment is concerned are calcium oxalate crystals derived from the squill extract, optionally with at least some of the mucilage associated therewith.

Further tests revealed, however that the active principle of such pharmaceutical compositions was a group Ia or IIa metal oxalate, optionally with an organic oxalate and/or mucilage derived from a plant extract.

In canadian patent 888689 there is disclosed the use of a composition for the treatment for the scalp against hair loss which essentially requires the use of an emulsion comprising bergamot oil, water and a ferrous salt including a ferrous oxalate (i.e. a group VIII metal salt).

GB-A 1568856 and FR-A-2347049 relate to compositions for the treatment of the hair and suggest an extract of red squill including a scilleroside as the active ingredient.

(a) WO-A-91/04007 relates to a conditioning activator for a no-lye hair relaxer including a water-soluble cationic compound as a conditioning agent for the hair.

JP-A-2247299 relates to a neutral liquid cleanser composition for use with tableware which is also soft on the skin which comprises inter alia a water soluble salt which may be a sodium or potassium oxalate.

JP-A-2133208 relates to a method of modifying keratin fibre by applying thereto a water soluble substance which forms a water insoluble or slightly soluble salt on contact with keratin. This is a two-part composition, one part of which may be calcium oxalate. The so-treated keratin fibre is more durable.

JP-B-54006612 relates to a solution for removing permanent waves from the hair. The solution comprises inter alia a sodium or potassium oxalate, but is specifically for the reversal of a permanent wave that has been formed by a chelate-forming metal oxide method.

Finally, JP-A-59139313 relates to a hair treating composition to maintain the set of the hair, one of many components in this composition being sodium oxalate.

The applicant has now found that in neither of Canadian 888689 or GB-A-1568856 was the active principle defined. It was in fact an oxalate and particularly a group IA or IIa metal or ammonium oxalate. In the case of the first Canadian disclosure the active principle may in fact have been a ferrous oxalate salt but was not defined as such, and tests have shown that said ferrous salt was generally ineffective on its own. Similarlly in the second GB or FR disclosure the oxalate was not specifically mentioned as a component of red squill.

Accordingly the first aspect of the present invention provides a pharmaceutical composition for restoration of hair loss by topical administration to the scalp or skin which comprises a pharmaceutically acceptable oxalate of a Group Ia or IIa metal or ammonium oxalate or a tricologically active derivative thereof disposed in a topically applicable pharmaceutically acceptable carrier or diluent therefore.

The carrier or diluent may be aqueous and/or alcoholic and may include a viscous base to retain the composition in situ in use. A suitable diluent is water or an alcohol such as isopropanol and/or for propylene glycol to form a lotion. To form a cream or ointment a paraffinic fraction and an emulsion base may be used.

In a second aspect of the present invention there is provided a composition for hair restoration which comprises an oxalate of a group Ia or IIa metal or ammonium oxalate, in a presence of a mucilaginous carbohydrate mass which may be derived from an extract of squill. The carbohydrate mass may comprise an organic oxalate.

One mucilaginous carbohydrate has been designated Sinstrin (page 767/768; A Modern Herbal; Mrs. M. Grieve). Further it has been found that generally in squill extracts calcium oxalate appears as crystals which pierce and intensely irritate the skin. Calcium oxalate crystals should therefore be crushed to a fine particle size at least, prior to use whether or not used in conjunction with the carbohydrate mucilage.

The pharmaceutically acceptable carrier or diluent may be water or an aqueous alcoholic solution, said alcohol being a lower alcohol (i.e. $C_3$ to $C_4$ alcohol) for example glycerol or isopropanol. For an ointment various proportions of the group Ia or IIa metal oxalate, or ammonium oxalate, mucilage, water and alcohol or ointment base may be selected for maximum effect on a trial and error basis. The composition containing the principal is preferably in a semi solid or semi liquid form containing one or more of the active compounds. Generally the active principle is included in a lotion or ointment at 0.1–10% by weight but generally in the order of 1–5% by weight. Amounts of up to 10% or more may be utilised in some circumstances under medical supervision, The pharmaceutical compositions contemplated by this invention include pharmmceutical compositions adopted for topical application to the human scalp and/or skin.

Conventional pharmaceutical forms for this purpose include ointments, lotions, pastes, jellies, gels, mousses, sprays, foams, aerosols and other similar The term "ointment" includes creams having oleaginous watersoluble emulsion bases, e.g. lanolin, petrolatum, glycols, glycerin, and similar.

The compounds may be lipsomal preparations or lipid emulsions or dissolved in conventional solvents such as acetonitrile, dimethylformamide (DMF), DMA, alcohol, propanol, and similar.

The percentage by weight of the oxalates utilised typically range from about 0.1% to about 10% of the pharmaceutical preparation, preferably from 0.75% to about 4.95% and in those preparations the aforesaid pharmaceutical carrier is utilised for topical application, and it is recommended to be used on a regular basis, and for a period of time sufficient to effect hair growth.

The percentage of the active ingredient as well as the frequency of the application may be varied according to the individual objective e.g.

1) To stimulate hair and prevent hair loss it is recommended to utilise 0.45% to about 0.95% of oxalates in the preparation.

2) For alopecia areata treatment it is recommended the use about 1.75% to about 2.75% of the selected oxalate twice a day.

3) For use in treating human baldness it is recommended to use from about 1% to about 1.75% of the selected oxalate in a topical solution or cream. A period of up to 2–7 months is required before evidence of hair growth stimulation can be confirmed. This can vary considerably among patients.

The invention will now be described by way of illustration only in the following examples:

EXAMPLE I

The squill plant is a perennial plant with fibrous roots extending from the base of a large truncated nearly globular bulb 10 to 15 cm long with dark green leaves which when fully grown is about 60 cm long. Whereas the plant differs greatly in size and colour its two significant varieties, red and white squill, are distinguished by the colour of the bulb scales.

The inner scales have mucilaginous bitter acid taste exhibiting the presence of bitter glucosides capable of causing direct inflammation of the skin.

PREPARATION OF THE MUCILAGE

The bulb of the squill plant is macerated into 3 mm pieces and 100 g of this finely chopped bulb is added to an air-tight container with at least 150 ml of isopropanol BP (or more of the alcohol until all pieces are covered). The container is then left to stand at room temperature for seven days and stirred occasionally. The macerated squill pieces are then further treated to produce a mass of squill mucilage. 50 ml of sterile water is then added to the residue and it is allowed to stand for a further one to two weeks with occasional shaking and stirring.

The resultant admixture is then sieved utilising a medium size sieve and the resultant filtrate and mucilage is kept without stirring for a period of one to two further weeks to allow the mucilage to settle at the bottom of the container. 80% of the isopropanol and water is then discarded and the remaining 20% is mixed with the mucilage.

The mucilage is mixed with one part of propylene glycol and one part sterile carbonated water and left for up to two weeks with stirring.

Calcium oxalate forms as needle shaped crystals. The calcium oxalate is important in that it appears to be the principle active ingredient. It may be utilised optionally with a proportion of the mucilage associated therewith and it is not therefore necessary to entirely separate all the mucilage from the calcium oxalate.

The separated mucilaginous calcium oxalate extract is then subjected to a grinding or crushing step utilising for example a pestle and mortar to achieve a final composition in which the calcium oxalate is in fine particulate form to avoid the oxalate needles irritating the skin.

VEHICLES AND DILUENTS

The vehicle or diluent may take the form of an ointment, cream or lotion. The vehicle is important in a treatment since excessive dilution may affect the stability of some creams and of course it is necessary to maintain contact of the active principle in accordance with the present invention with the scalp or hair which is intended to be restored and revitalised.

These cream and ointment bases may have both hydrophillic and/or lipophilic properties.

Depending upon the size of the effected area and the severity of scalp and hair disorder in the individual case, the recommended application rate for the composition is 1–10% by weight. Amounts over 5% may be utilised only under medical supervision. Care should of course be taken to prevent any microbial contamination or contact of the composition with the eyes of a recipient. Citric acid, preferably as lime juice, may reduce the irritation which is caused when the composition disposed in an aqueous vehicle is applied to the afflicted part. No side effects or instability of the applied composition have been observed.

EXAMPLE II

An ointment composition in accordance with the invention was formed as follows:

| | |
|---|---|
| White soft paraffin BP | 15.0% |
| Light liquid paraffin PHEUR | 13.0% |
| Hypoallergenic anhydrous lanolin | 1.0% |
| Emulsion base | 60.0% |
| Squill derived calcium oxalate with approx. equal weight of mucilage | 6.0% |
| Citric acid | 5.0% |

EXAMPLE III

A composition in accordance to the invention was formed as follows:

| | |
|---|---|
| White soft paraffin BP | 15.0% |
| Light liquid paraffin PHEUR | 13.0% |
| Hypoallergenic anhydrous lanolin | 1.0% |
| Emulsion base | 67.0% |
| Calcium oxalate B.P. as a fine powder | 4.0% |

EXAMPLE IV

A composition in accordance with the invention was found as follows:

| | |
|---|---|
| White soft paraffin BP | 15.0% |
| Light liquid paraffin PHEUR | 13.0% |
| Hypoallergenic anhydrous lanolin | 1.0% |
| Emulsion base | 68.5% |
| Citric acid | 0.5% |
| Magnesium oxalate B.P. as a fine powder | 2.0% |

EXAMPLE V

A composition in accordance with the invention was formed as follows:

| | |
|---|---|
| White soft paraffin BP | 15.0% |
| Light liquid paraffin PHEUR | 13.0% |
| Hypoallergenic anhydrous lanolin | 1.0% |
| Emulsion base | 68.5% |
| Potassin oxalate B.P. | 1.5% |
| Ammonium oxalate B.P. | 1.0% |

EXAMPLE VI

An aqueous cream comprising by weight:

| | |
|---|---|
| Phenoxethanol | 1% |
| Emulsifying ointment | 30% |
| Water | 66% |
| Calcium oxalate B.P. | 2% |
| Citric acid | 1% |

EXAMPLE VII

Each of the compositions shown in examples II–VI were applied as ointments twice daily to the scalp of a group of five patients. E45, a propriety anti-dermatitis cream, was applied as a control to a separate group. The ointment was applied twice daily initially to the affected areas for the first week, reducing to once a day or less frequently as the respective conditions improved. The ointment was applied sparingly over the afflicted area. It was found that as against the control group, treatment with the composition containing the calcium oxalate resulted in hair growth after about three weeks, whereas there was no significant hair growth in the control group.

There appeared to be no significant statistical difference between the results obtained with the invention in accordance with examples II to V; all working equally well.

EXAMPLE VIII

Further a lotion was prepared consisting of 3% by weight of calcium oxalate, 0.5% citric acid disposed in 40% by weight of propylene glycol; the balance being isopropanol to 100% by weight. This was applied to the hair and scalp twice a day.

Hair growth occurred gradually as the scalp was cleared by the lotion, although some of the hair regrowth tended to be lighter in colour or even white. There was some evidence that the original colour started to return after a few months.

The difficulties with the application of lotion are that there is a tendency for the lotion to run into the eye and for the oxalate, which may be only partially in solution, to leave the afflicted area fairly quickly resulting in lower treatment benefits. It is for this reason the ointment is to be preferred.

In the present invention, as the scaling (dandruff) is diminished, the general appearance of the hair and scalp improves, and new hair growth is evident.

It is apparent that after a few days of using the present pharmaceutical composition, any problematic condition on the scalp or skin seems to be receding and the skin/scalp is found to be healthy and without abnormal scale formations, it is evident that the present composition/s has a cleansing effect on the skin, while it results in curing alopecia arcata, male patern baldness, or any other forms of hair loss, while the skin is kept not too greasy or too dry.

It has been observed that when oxalate solution was applied only on one particular area of the scalp, on some occasions that application assisted other parts of the scalp to promote new growth of hair.

The invention relates therefore to a pharmaceutical composition for the treatment of the hair and for a method of enhancing the aesthetic appearance of the scalp and skin.

I claim:

1. A pharmaceutical composition for restoration of hair loss by topical administration to the scalp or skin which comprises a pharmaceutically acceptable oxalate of a Group Ia or IIa metal or ammonium oxalate or a tricologically active derivative thereof disposed in a topically applicable pharmaceutically acceptable carrier or diluent therefor, wherein the oxalate is derived from a vegetable extract, and is associated with mucilaginous carbohydrate derived from said vegetable extract.

2. A composition according to claim 1 wherein the pharmaceutically acceptable oxalate is an oxalate of a metal selected from calcium, barium, magnesium, lithium, sodium or potassium.

3. A composition according to claim 1 wherein the pharmaceutically acceptable carrier or diluent comprises at least one of a $C_3$ to $C_4$ lower alcohol and sterile water.

4. A composition according to claim 1 wherein the pharmaceutically acceptable carrier or diluent comprises a paraffin fraction and an emulsion base.

5. A composition according to claim 1 wherein the oxalate is calcium oxalate derived from an extract of squill.

6. A composition according to claim 1 further comprising an organic oxalate.

7. A method for enhancing the aesthetic appearance of the scalp or skin which comprises applying to the scalp or skin a composition which comprises a pharmaceutically acceptable oxalate of a Group Ia or IIa metal or ammonium oxalate or a tricologically active derivative thereof disposed in a topically applicable pharmaceutically acceptable carrier or diluent therefor.

8. A method for the restoration of hair loss which comprises applying topically to the scalp or skin a pharmaceutical composition comprising a pharmaceutically acceptable oxalate of a Group Ia or IIa metal or ammonium oxalate, or a tricologically active derivative thereof, disposed in a topically applicable pharmaceutically acceptable carrier or diluent therefor.

9. A method according to claim 8 wherein the pharmaceutically acceptable oxalate is an oxalate of a metal selected from calcium, barium, magnesium, lithium, sodium or potassium.

10. A method according to claim 8 wherein the pharmaceutically acceptable carrier or diluent comprises at least one of a $C_3$ to $C_4$ lower alcohol and sterile water.

11. A method according to claim 8 wherein the pharmaceutically acceptable carrier or diluent comprises a paraffin fraction and an emulsion base.

12. A method according to claim 8 wherein the oxalate is derived from a vegetable extract.

13. A method according to claim 8 wherein the oxalate is calcium oxalate derived from an extract of squill and wherein the calcium oxalate is additionally surrounded by a mucilaginous carbohydrate.

14. A method according to claim 8 wherein the composition further comprises an organic oxalate.

* * * * *